(12) United States Patent
Arth et al.

(10) Patent No.: US 9,423,784 B2
(45) Date of Patent: Aug. 23, 2016

(54) SENSOR ARRANGEMENT FOR DETECTING A SAFE INSTALLATION STATE OF AN INSTALLATION OPERATED IN AN AUTOMATED MANNER

(71) Applicant: Pilz GmbH & Co. KG, Ostfildern (DE)

(72) Inventors: Christophe Arth, Seltz-Eberbach (FR); Erik Holzapfel, Ostfildern (DE); Martin Bellingkrodt, Ostfildern (DE)

(73) Assignee: PILZ GMBH & CO. KG, Ostfildern (DE)

( * ) Notice: Subject to any disclaimer, the term of this patent is extended or adjusted under 35 U.S.C. 154(b) by 638 days.

(21) Appl. No.: 13/778,370

(22) Filed: Feb. 27, 2013

(65) Prior Publication Data

US 2013/0233044 A1    Sep. 12, 2013

(30) Foreign Application Priority Data

Mar. 7, 2012    (DE) .......................... 10 2012 101 933

(51) Int. Cl.

| | | |
|---|---|---|
| G05B 19/048 | (2006.01) | |
| G05B 19/042 | (2006.01) | |
| G05B 9/03 | (2006.01) | |
| G01N 35/00 | (2006.01) | |

(52) U.S. Cl.
CPC ........ *G05B 19/048* (2013.01); *G01N 35/00584* (2013.01); *G05B 9/03* (2013.01); *G05B 19/0423* (2013.01); *G05B 19/0428* (2013.01); G05B 2219/24008 (2013.01)

(58) Field of Classification Search
CPC ............... G01N 35/00584; G05B 9/03; G05B 19/0423; G05B 19/0428; G05B 19/048; G05B 2219/24008
See application file for complete search history.

(56) References Cited

U.S. PATENT DOCUMENTS

| 6,409,083 B1 | 6/2002 | Link |
|---|---|---|
| 7,548,159 B2 | 6/2009 | Pullmann et al. |
| 7,656,629 B2 | 2/2010 | Pullmann et al. |

FOREIGN PATENT DOCUMENTS

| DE | 103 37 660 A1 | 6/2004 |
|---|---|---|
| DE | 103 34 653 A1 | 3/2005 |
| DE | 10 2004 020 997 A1 | 11/2005 |
| EP | 0 968 567 B2 | 1/2000 |

OTHER PUBLICATIONS

DIN EN 954-1, Safety-related parts of control systems Part 1: General principles for design, Mar. 1997, 34 pages.
EN ISO 13849-1, Safety of machinery—Safety-related parts of control systems—Part 1: General principles for design, Nov. 2006, 97 pages.
CEI IEC 61508-2, Functional safety of electrical/electronic/programmable electronic safety-related systems—Part 2: Requirements for electrical/electronic/programmable electronic safety-related systems, May 2000, 152 pages.

*Primary Examiner* — Paul West
(74) *Attorney, Agent, or Firm* — Harness, Dickey & Pierce, P.L.C.

(57) ABSTRACT

A sensor arrangement for detecting a safe installation state of an automated installation has an input circuit designed to receive a first input signal and at least one further input signal. The first input signal depends on the safe installation state to be detected. The further input signal depends on a further operational state. The sensor arrangement also has a first output and at least one second output and an evaluation unit for outputting a first output signal and a second output signal at the first and second outputs, respectively. The evaluation unit is designed to evaluate the first input signal in a failsafe manner and on the basis thereof produce a redundant signal pair at the first and second outputs to signal a safe installation state, and to evaluate the further input signal and on the basis thereof generate non-redundant output signals different from the redundant signal pair.

20 Claims, 2 Drawing Sheets

SENSOR ARRANGEMENT FOR DETECTING A SAFE INSTALLATION STATE OF AN INSTALLATION OPERATED IN AN AUTOMATED MANNER

CROSS REFERENCES TO RELATED APPLICATIONS

This application claims foreign priority under the Paris Convention from German patent application DE 10 2012 101 933.9 filed on Mar. 7, 2012 with the German Patent and Trademark Office. The entire content of this priority application is incorporated herein by reference.

BACKGROUND OF THE INVENTION

The present invention relates to a sensor arrangement designed for detecting and reporting to a higher level controller a safe installation state of an automatically operated installation.

DE 103 37 660 A1 discloses a sensor arrangement having an input circuit in the form of a so-called receiving head which is able to receive different input signals. The different input signals come from a plurality of transponders, each transponder emitting an individual identification signal when it enters the vicinity of the receiving head. An evaluation unit can use the identification signals to decide which transponder is in the vicinity of the receiving head at a particular time. The known sensor arrangement is used, in particular, to detect various operating positions of a movable part. In one example, the transponders are arranged on the lateral edge of a rolling door. Depending on the open or closed position of the rolling door, the receiving head receives a different transponder signal as an input signal. The evaluation unit can use the received transponder signal to determine the open or closed position of the rolling door and, on the basis thereof, can generate a control command for a motor control unit which is used to open or close the rolling door.

Controlling the rolling door on the basis of the detected position is a typical example of an automated process in which mechanical parts are moved. There are many cases in which the parts must be moved with a particular degree of accuracy. It is therefore necessary to determine the instantaneous position and/or other movement variables, for instance the movement speed. Any faults may disrupt the desired operating procedure. During the automated production of products, faults may affect, in particular, the product quality and/or the productivity.

In addition, there are cases in which the operating position of a movable part is relevant to safety, for instance in the case of a guard door which closes access to a dangerous machine. In such a case, it must be ensured that the machine cannot be activated if the guard door is open. Here, the accuracy of the position determination does not play a role as long as the closed guard door is reliably detected. On the other hand, a fault in the sensor arrangement must not, under any circumstances, result in the machine being able to be activated when the guard door is open.

From these different requirements, sensor arrangements and controllers have been developed either for the normal operating procedure of an automated installation or for safeguarding a dangerous machine. In practice, a distinction is often made between so-called standard applications, which relate to the usual operating procedure of an automated installation, and fail-safe applications which are primarily used to protect against dangerous machine movements or the like. Since a fault in a fail-safe application may endanger the health or even the life of persons, while faults in a standard application "only" affect the quality of products and/or the installation productivity, components and devices for fail-safe applications require special approval from supervisory authorities, which approval is only given if the intended safety function is also ensured in the case of any conceivable fault. Components for fail-safe applications therefore require a remarkably higher amount of design effort in order to achieve the required fail-safety in comparison with components and devices for standard applications. In addition, any change to a device or a component for a fail-safe application must be tested again by the supervisory authority since the change might be the cause of the loss of the required safety function in the event of a fault.

On account of the higher requirements imposed on fail-safety, a distinction has been made to date between devices and components for standard applications and devices/components for fail-safe applications. However, the sensor arrangement from DE 103 37 660 A1 mentioned above makes it possible to combine a standard application (namely determination of the current operating position of the rolling door in order to control movement) with a safety function (namely fail-safe detection of the completely closed door). In order to maintain separation between standard application and fail-safe application, DE 103 37 660 A1 proposes an evaluation unit which internally has a standard part and a separate fail-safe part. The input signals from the different transponders are supplied to the parts in a parallel manner. However, the output signals from the evaluation unit are clearly separate for standard applications and fail-safe applications.

The known sensor arrangement therefore makes it possible to use a single sensor part which is designed to receive different identification signals, with one of the identification signals being a safety-relevant signal for a fail-safe application, while the other signals are standard signals for controlling an operating procedure in a manner which is not relevant to safety.

DE 10 2004 020 997 A1 discloses a sensor arrangement which is exclusively intended for fail-safe applications. This known sensor arrangement also has an input circuit for receiving a signal which comes from a transponder. The sensor arrangement has a redundant design and has two microcontrollers which monitor one another. Two switching elements generate redundant output signals. This sensor arrangement can be used to monitor the closed position of a guard door, with the redundant output signals only together signaling the safe closed position of the guard door. A similar two-channel sensor arrangement for fail-safe applications is disclosed by EP 0 968 567 B2.

DE 103 34 653 A1 discloses another sensor arrangement for monitoring a guard door in a fail-safe manner. In this case, a switching element is arranged in the input circuit for receiving the signal from a transponder, which switching element can selectively be used to suppress the input signal from the transponder. The switching element thus enables regular functional tests which ensure fault-free operation of the sensor.

SUMMARY OF THE INVENTION

Against this background, it is an object of the present invention to provide an alternative sensor arrangement which can be used both for standard applications and for fail-safe applications. It is another object to provide such a sensor arrangement which can be implemented in a cost-effective manner. It is yet another object to provide such a sensor arrangement which has a small and compact structure.

According to one aspect of the invention, in an installation operated in an automated manner under the control of at least one control unit, said installation having a plurality of operational states and at least one safety-related state, there is provided a sensor arrangement comprising an input circuit designed to receive a first input signal depending on the safety-related state and designed to receive at least one further input signal depending on one of said plurality of operational states, comprising a first output and at least one second output for outputting a first output signal and a second output signal to the at least one control unit, and comprising an evaluation unit designed to evaluate the first input signal in a fail-safe manner and, on the basis thereof, to generate the first and second output signals at the first and second outputs, with the first and second output signals forming a redundant signal pair which in combination signals the safety-related state to the control unit, and wherein the evaluation unit is further designed to evaluate the further input signal and, on the basis thereof, to generate a third output signal at the first output and a fourth output signal at the second output, with the third and fourth output signals forming a non-redundant signal pair which differs from the redundant signal pair.

According to another aspect, there is provided a sensor arrangement for detecting a safe installation state of an installation operated in an automated manner, the sensor arrangement comprising an input circuit designed to receive a first input signal and designed to receive at least one further input signal, with the first input signal depending on the safe installation state to be detected, and with the further input signal depending on a further state, comprising a first output and at least one second output for outputting a first output signal and a second output signal, and comprising an evaluation unit designed to evaluate the first input signal in a fail-safe manner and, on the basis thereof, to generate the first and second output signals at the first and second outputs, with the first and second output signals forming a redundant signal pair which in combination signals the safe installation state, wherein the evaluation unit is further designed to evaluate the further input signal and, on the basis thereof, to generate a third output signal at the first output and a fourth output signal at the second output, with the third and fourth output signals forming a non-redundant signal pair which differs from the redundant signal pair.

The novel sensor arrangement is a fail-safe sensor arrangement designed for fail-safe applications in terms of machine safety, since it has an evaluation unit which is designed to evaluate the first input signal in a fail-safe manner and, on the basis thereof, to generate a redundant signal pair. In this context, "fail-safe", as used herein and in the claims, means that the sensor arrangement is designed such that it complies with category 3, SIL3 or performance level PL d according to the relevant standards EN 954-1, IEC 61508, ISO 13849, or with similar standards for failsafe applications. On the other hand, the terms "operational state(s)" or "standard operational state(s)," as used herein as well as in the claims, refer to the non-safety related, normal operating procedures of an automated machine or installation.

The redundant signal pair comprises a first output signal at the first output and a second output signal at the second output, these two signals each carrying the same information. In principle, one of the output signals would therefore suffice to signal a safe state to a higher level controller on the basis of the first input signal. However, it is generally possible that one of the output signals assumes a signal level which could incorrectly signal the safe state as a result of a fault, such as a transistor which has broken down or a short circuit to a voltage potential. Therefore, the novel sensor arrangement has the second output, and the first and second output signals only together signal the safe installation state.

In addition, the evaluation unit of the novel sensor arrangement is also designed to evaluate the further input signal and, on the basis thereof, to generate a third output signal at the first output and a fourth output signal at the second output. The third and fourth output signals form a non-redundant signal pair, i.e. they do not carry the same information. In addition, the non-redundant signal pair, formed by the third and fourth output signals, differs from the redundant signal pair. A higher level controller can therefore discern whether or not the signal pair provided at the first and second outputs signals a safe installation state, i.e. whether or not the evaluation unit generates the first and second output signals at the first and second outputs. However, in the last-mentioned case, the sensor arrangement can use the third and fourth output signals to signal states which are not relevant to safety, for instance a non-safety-relevant operating state of a movable part. Both the redundant signal pair and the non-redundant signal pair are provided at the first and second outputs.

In other words, the evaluation unit of the novel sensor arrangement is able to use the first and second outputs both for a fail-safe application and for a standard application. The novel sensor arrangement can therefore be used either for fail-safe applications and/or for standard applications. In particular, it is possible to use the first output and the redundant second output as non-redundant individual outputs. Therefore, in comparison with known fail-safe sensor arrangements, the novel sensor arrangement has an extended range of functions. The extended range of functions includes the redundant outputs being used as unsafe individual outputs on the basis of a non-safety-relevant (further) input signal. On the basis of the further input signal, the evaluation unit generates an information-carrying third output signal or an information-carrying fourth output signal at only one of the redundant safety outputs. The respective other safety output is occupied by a defined output signal which ensures that confusion with the redundant signal pair, which in combination signals the safe installation state, is avoided.

The novel sensor arrangement can be implemented in a cost-effective manner and with a very small structure since the evaluation unit required for the fail-safe application is now also used for the standard application. In addition, the novel sensor arrangement does not require any additional outputs for the standard signals. The above-mentioned object is therefore completely achieved.

In a preferred refinement, the evaluation unit generates the redundant signal pair with the first and second output signals only when the input circuit receives only the first input signal.

In this refinement, the evaluation unit generates the redundant signal pair, if and only if the input circuit receives exclusively the first input signal. If a further input signal is received in addition to the first input signal, the evaluation unit does not generate the redundant signal pair even if the first input signal is also received. This refinement ensures that the safety-relevant redundant signal pair is output only when the sensor arrangement operates as a pure fail-safe application. The refinement includes that the evaluation unit does not carry out any AND operation between the first input signal and the further input signal. The redundant signal pair depends only on the first input signal. The refinement has the advantage that the safety function of the novel sensor arrangement is unchanged in comparison with known fail-safe sensor arrangements. The further input signal is prevented from influencing the safety function. This refinement consequently enables cost-effective compatibility with known sensor arrangements for fail-safe applications, but with the now extended range of functions.

In another refinement, the output signals at the first and second outputs each are binary signals which have either an active first signal level or a passive second signal level, with the first and second output signals each having the active first signal level.

In this refinement, the first and second output signals, which together form the redundant signal pair, each have the active signal level at least temporarily. The active signal level requires an operating voltage and corresponding activation of the sensor arrangement. In comparison with this, the passive signal level in some exemplary embodiments may be a signal level which corresponds to the signal level at the first and second outputs when the sensor arrangement is switched off. However, in other exemplary embodiments, it is possible for the passive second signal level to also differ from a "non-existent" output signal. In some exemplary embodiments, the active first signal level is a positive voltage which is related to and which considerably distinguishes from a reference potential, and the passive second signal level is a voltage which approximately corresponds to the reference potential. In some exemplary embodiments, the output signals at the first and second outputs may be clocked binary signals which alternately assume the active first signal level or passive second signal level. The refinements have the advantage that the safe installation state can be signaled with the aid of the first and second output signals only when the evaluation unit specifically generates the first and second output signals. A so-called "quiescent current principle" which is preferred for fail-safe applications is thus implemented.

In another refinement, the third output signal or the fourth output signal corresponds to the passive second signal level.

In this refinement, one of the two output signals of the non-redundant signal pair has the passive second signal level permanently or at least largely permanently. In other words, the corresponding output is virtually "switched off". In contrast, the first and second output signals in the preferred exemplary embodiments each have the active first signal level. The refinement is a simple and cost-effective possibility for reliably distinguishing the output signals for standard applications from the safety-relevant output signals for fail-safe applications.

In another refinement, the first and second output signals have regularly changing signal levels.

In some preferred exemplary embodiments, the first and second output signals are clock signals with a defined and preferably fixed period/frequency. In some exemplary embodiments, the first and second output signals each have a different clock frequency and/or phase angle. These refinements use dynamic output signals to signal a safe installation state. Since dynamic signals with a defined period duration/frequency are not "randomly" produced, these refinements provide increased fail-safety. Short-circuits of the signal lines on which the first and second output signals are transmitted can be detected more easily if the clock signals have different frequencies and/or phase angles.

In another refinement, the evaluation unit generates the redundant signal pair and the non-redundant signal pair in temporally successive intervals.

In this refinement, the novel sensor arrangement enables a time slot method for transmitting the redundant signal pair and the non-redundant signal pair. For example, the redundant signal pair can be generated—on the basis of the first input signal—in periodic intervals of time which are adapted to a processing cycle of a higher level safety controller. The third and fourth output signals can be transmitted between the intervals of time for transmitting the redundant signal pair. This refinement also includes the non-redundant signal pair being generated after the redundant signal pair has been cancelled, for instance in order to send a standard control command to the higher level controller after the installation has been switched off. The refinement enables the combined use of the novel sensor arrangement both for a standard application and for a fail-safe application with a small number of lines between the sensor arrangement and the higher level controller.

In another refinement, the novel sensor arrangement has a first device housing, in which the input circuit and the evaluation unit are arranged, and at least one actuator which is spatially separate from the first device housing and generates one of the input signals. The actuator preferably generates the first input signal.

This refinement enables a very robust sensor arrangement which is designed to detect the operating position of a moving part. Such sensor arrangements are required both for standard applications and for fail-safe applications. The sensor arrangement of this refinement is suitable, in particular, for detecting operating positions which are important both for a standard application and for a fail-safe application. This refinement accordingly enables a particularly cost-effective implementation for such applications.

In another refinement, the actuator has an individual identification code which is transmitted to the evaluation unit via the at least one input signal.

In this refinement, the actuator comprises a transponder, in particular an RFID transponder. The input circuit comprises a reading head for reading the identification code. The refinement provides increased safety and security against manipulation and easy distinction between different input signals.

In another refinement, the at least one actuator comprises a first actuator with the individual identification code and at least one further actuator with a further individual identification code, with the evaluation unit distinguishing the first input signal from the further input signal on the basis of the first individual identification code and the further individual identification code.

In this refinement, the first input signal and the further input signal each are signals which differ substantially by their individual identification code only. In preferred exemplary embodiments, the sensor arrangement comprises a first transponder in the first actuator and a further transponder in the further actuator, with the evaluation unit using the identification codes to detect whether the first input signal or the further input signal is involved. This refinement makes it possible to use the first actuator for the fail-safe application, while the further actuator is used for a standard application. Adaptation of the sensor arrangement to different applications is very simple and cost-effective in this refinement.

In another refinement, the evaluation unit integrates the individual identification code in at least one of the output signals.

In this refinement, the individual identification code is contained in at least one of the output signals. In this manner, the novel sensor arrangement can provide a higher level control unit with the individual identification code. In combination with binary signals, the refinement has the advantage that the integration of the individual identification code results in a dynamic output signal, which is advantageous with regard to fail-safe applications.

In another refinement, the input circuit has a cable connection for supplying the further input signal.

In this refinement, the novel sensor arrangement has a connection which can be used, for example, for a pushbutton which can be used by an operator to generate a non-safety-relevant acknowledgement signal for a higher level controller. The sensor arrangement in this refinement therefore makes it possible to connect simple signaling devices to a higher level controller in a cost-effective manner, with the redundant outputs of the fail-safe sensor arrangement being "converted to another purpose" for transmitting standard signals.

It goes without saying that the features mentioned above and the features yet to be explained below can be used not only in the respectively stated combination but also in other combinations or alone without departing from the scope of the present invention.

BRIEF DESCRIPTION OF THE DRAWINGS

Exemplary embodiments of the invention are illustrated in the drawing and are explained in more detail in the following description. In the drawing.

DESCRIPTION OF PREFERRED EMBODIMENTS

Figure 1:
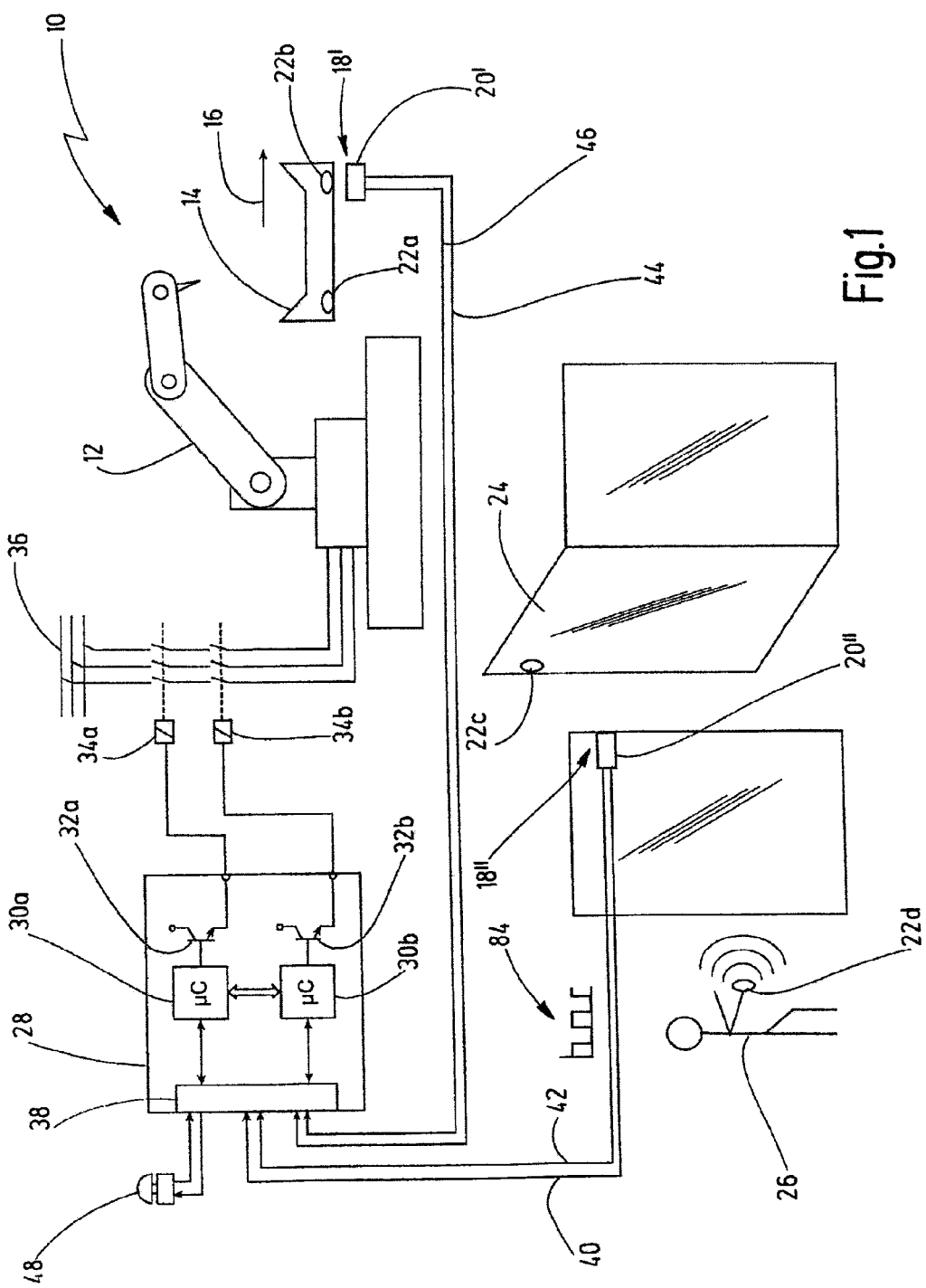
FIG. 1 shows a simplified illustration of an automated installation having an exemplary embodiment of the novel sensor arrangement.

In FIG. 1, an installation having a plurality of exemplary embodiments of the novel sensor arrangement is denoted in its entirety by reference numeral 10. In this case, the installation 10 comprises a robot 12 which deposits workpieces (not illustrated here) into a transport carriage 14. The transport carriage 14 can be moved in the direction of arrow 16, for instance in order to supply the workpieces to a further robot (not illustrated here). The installation 10 is only illustrated by way of example here and shows only one of many applications for the novel sensor arrangement.

Reference numeral 18' is used to denote an exemplary embodiment of the novel sensor arrangement. The sensor arrangement 18' has a sensor part 20' and a plurality of actuators 22a, 22b which are spatially separate from the sensor part 20'. In the example shown here, the actuators 22a, 22b are arranged at different positions on the transport carriage 14. The sensor part 20' is able to detect the presence of an actuator 22a, 22b when the corresponding actuator enters the vicinity of the sensor part 20'. If the distance between the actuator 22a and the sensor part 20' is too large, the sensor part 20' may not detect the actuator, which applies to the actuator 22a in the case illustrated in FIG. 1. The sensor part 20' can use the actuators 22a, 22b to detect which end of the transport carriage 14 is in the region of the sensor part 20' at a defined time. Such information is important for controlling the operating procedure of the installation 10, that is to say a standard application in which the position of the transport carriage 14 is determined using the sensor arrangement 18'.

The movements of the robot 12 are often so quick that they are dangerous to people in the working area of the robot 12. The working area of robots is therefore generally protected with guard fences and guard doors. The guard doors allow access to the working area of the robot 12 in order to eliminate a fault. During normal operation, however, the guard door must be closed in order to avoid endangering people.

Reference numeral 24 denotes such a guard door, the closed position of which is monitored with a further sensor arrangement 18" here. A further actuator 22c is arranged on the guard door 24. The sensor part 20" of the sensor arrangement 18" can detect a signal (not illustrated here) generated by the actuator 22c only when the guard door 24 is closed and the actuator 22c is accordingly in the vicinity of the sensor part 20".

In the exemplary embodiment illustrated here, the sensor arrangement 18" comprises a further actuator 22d which is held by an operator 26 here. The actuator 22d can be used, for example, to transmit a non-safety-relevant signal to a higher level controller 28 via the sensor arrangement 18". In other exemplary embodiments, however, the sensor arrangement 18" is used solely to monitor the closed position of the guard door 24, that is to say the actuator 22d is dispensed with in these cases.

The controller 28 is illustrated here in the form of a safety controller which has a plurality of redundant signal processing channels 30a, 30b. The controller 28 accordingly has at least two redundant switching elements 32a, 32b. The signal processing channels 30a, 30b process input signals of the controller 28 and, on the basis of the input signals, generate control signals which are used to drive actuators in the installation 10. These actuators here include two contactors 34a, 34b, the normally open contacts of which are arranged in series between a power supply 36 and electrical drives of the robot 12. The controller 28 can use the contactors 34a, 34b to interrupt the power supply for the robot 12 in a fail-safe manner.

Protection against a dangerous machine, such as the robot 12 here, is often achieved with the aid of a safety controller specially designed for the fail-safe application, while the operating procedure, i.e. the standard application, is controlled with the aid of a separate, non-fail-safe operation controller. However, there are also cases in which a safety controller also implements the standard application in addition to the fail-safe application. A suitable controller is, for example, the fail-safe controller PSS® 4000 from Pilz GmbH & Co. KG, Osffildern, Germany.

The controller 28 has an interface part 38 to which input signals can be supplied and at which (further) output signals can be provided. The outputs of the switching elements 32a, 32b which are used to drive the redundant contactors 34a, 34b are typically also part of the interface part 38, the illustration here being selected for reasons of clarity.

In the exemplary embodiment illustrated, the sensor part 20" of the sensor arrangement 18" is connected to the interface part 38 of the controller 28 via a first line 40 and a second line 42. The sensor part 20" provides, via the lines 40, 42, two output signals which are supplied to the controller 28 as (safety-relevant) sensor signals.

The sensor part 20' of the sensor arrangement 18' is connected to the interface part 38 of the controller 28 via two further lines 44, 46. Via the lines 44, 46, the sensor part 20' provides two output signals for the controller 28, which output signals represent an operating position of the transport carriage 14.

The method of operation of the installation 10 is as follows: the controller 28 reads in the output signals from the sensor arrangement 18' in defined, recurring intervals of time via the lines 44, 46 and determines the current operating position of the transport carriage 14 with the aid of the signals which have been read in. On the basis thereof and on the basis of further input signals (not illustrated here), the controller 28 generates control signals for actuators which are used to move the robot 12 and the transport carriage 14 in order to implement a desired operating procedure. This control circuit implements a standard application.

The controller 28 also reads in the output signals from the sensor arrangement 18", which are provided by the sensor arrangement 18" via the lines 40, 42, in defined, recurring intervals of time. The controller 28 can read in further input signals from other sensors, as is illustrated here, for example, by means of emergency stop button 48. The redundant signal processing channels 30a, 30b evaluate the output signals from the sensor arrangement 18" and from the emergency stop button 48 and drive the switching elements 32a, 32b on the basis thereof. The robot 12 is connected to the power supply 36 via the contactors 34a, 34b only when the guard door 24 is closed and the emergency stop button 48 has not been actuated.

Figure 2:
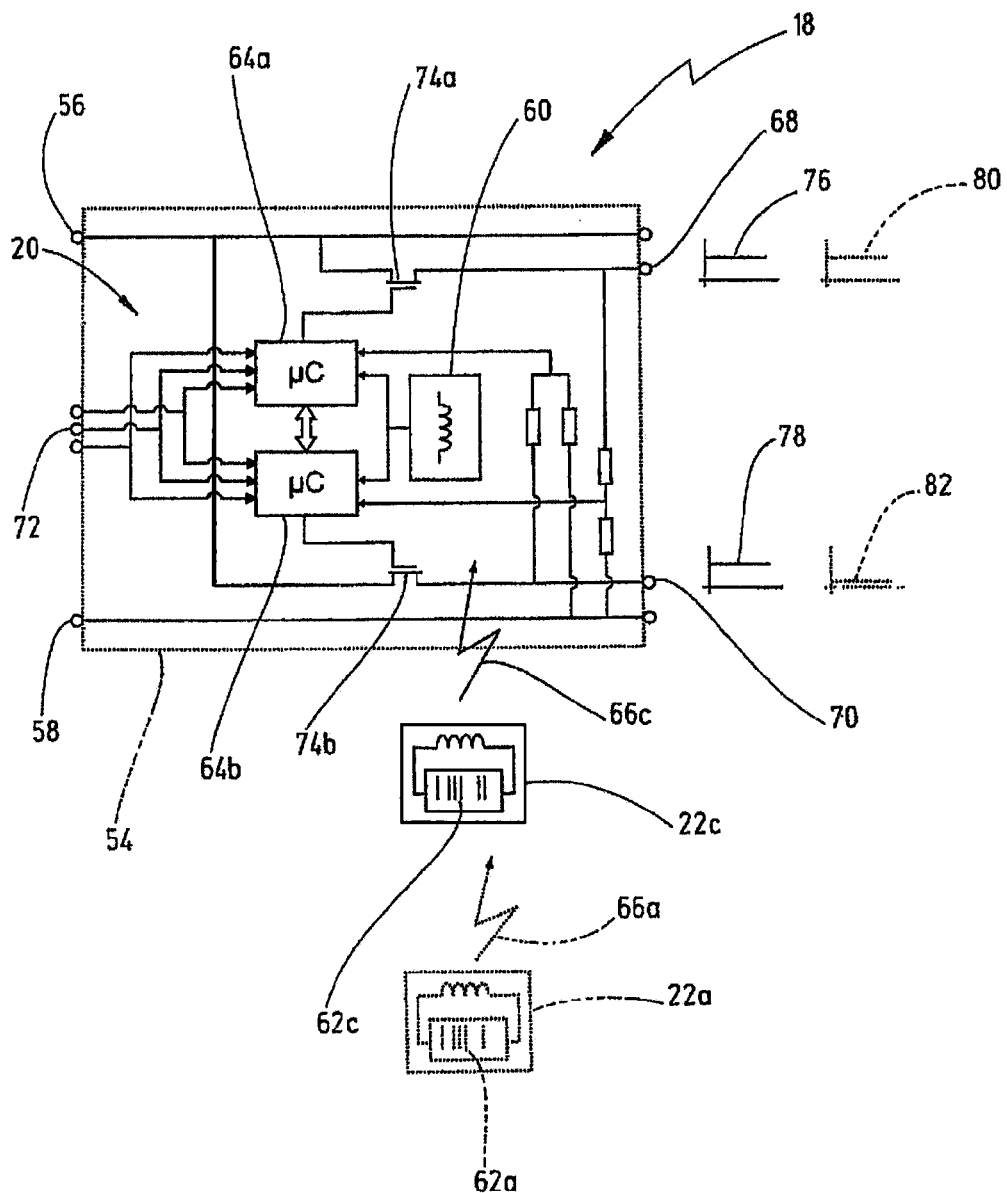
FIG. 2 shows an exemplary embodiment of the sensor arrangement in the installation according to FIG. 1.

FIG. 2 shows an exemplary embodiment of the novel sensor arrangements 18', 18". In the preferred exemplary embodiments, the sensor parts 20', 20" of the sensor arrangements 18', 18" are identical, with the result that a common stock of spare parts can be kept available for the sensor arrangement 18' (standard application) and the sensor arrangement 18" (fail-safe application). Accordingly, a distinction is no longer made between the sensor arrangements 18', 18" in the following description.

The sensor arrangement 18 has a device housing 54 in which the sensor part 20 is arranged. In some exemplary embodiments, the device housing 54 is injection molded or is closed in a water-proof manner in another suitable manner. Connection pins which make it possible to electrically connect the sensor arrangement 18 are arranged on the device housing 54. In the exemplary embodiment illustrated, a connection pin 56 is used to supply an operating voltage and a connection pin 58 is used to supply an operational ground to which the operating voltage is related. The reference numeral 60 is used to denote an input circuit for receiving input signals. In the preferred exemplary embodiment, the input circuit 60 comprises a reading head for reading a transponder. The actuators 22a, 22c each comprise a transponder with an individual identification code which is illustrated in a simplified manner in FIG. 2 at the reference numerals 62a, 62c. Each transponder generates a signal containing the respective identification code. The input circuit 60 receives the transponder signals as input signals and provides two microcontrollers 64a, 64b with the respective identification code. The microcontrollers 64a, 64b together form an evaluation unit which evaluates the respective input signal 66a, 66c from the actuators 22a, 22c in a fail-safe manner and, on the basis thereof, provides output signals at connection pins 68, 70. The connection pins 68, 70 are connected to the higher level controller 28 via the lines 40, 42 or 44, 46 (see FIG. 1).

Instead of microcontrollers, the novel sensor arrangement 18 may have other signal processing circuits, for example in the form of FPGAs, ASICs, among others. It is also possible to design the evaluation unit in a fail-safe manner with only one signal processing channel, as described in DE 103 34 653 A1 mentioned at the outset. This document is incorporated herein by reference.

In the preferred exemplary embodiments, the sensor arrangement 18 also has at least one further connection pin 72 which can be used to supply an external enable signal to the evaluation unit 64a, 64b. Such an enable signal makes it possible to advantageously connect sensors in series, as is described in DE 10 2004 020 997 A1 which was mentioned at the outset and is also incorporated herein by reference.

On the basis of the input signal 66a or 66c and possibly on the basis of one or more enable signals at the connection pins 72, the evaluation unit 64a, 64b drives two redundant switching elements 74a, 74b. The evaluation unit 64a, 64b uses the switching elements 74a, 74b to generate the output signals at the connection pins 68, 70.

If the evaluation unit 64a, 64b receives the input signal 66c from the actuator 22c on the guard door 24, the evaluation unit 64a, 64b generates a first output signal 76 and a second output signal 78 which together form a redundant signal pair which signals the safe installation state "closed guard door". As illustrated in a simplified manner in FIG. 2, the output signals 76, 78 in the preferred exemplary embodiments each have a voltage level corresponding approximately to the operating voltage. In further exemplary embodiments, the first and second output signals 76, 78 may have alternating signal levels at a defined frequency, as is illustrated in a simplified manner at reference numeral 84 in FIG. 1. In these cases, the first and second output signals preferably have different frequencies and/or phase angles in order to make it possible for the higher level controller 28 to carry out a short-circuit test.

In contrast, if the evaluation unit 64a, 64b receives the input signal 66a from the actuator 22a, it generates a third output signal 80 and a fourth output signal 84 at the connection pins 68, 70 with the aid of the switching elements 74a, 74b. The third and fourth output signals 80, 82 form a non-redundant signal pair which differs from the redundant signal pair 76, 78. For example, the evaluation unit 64a, 64b generates the third output signal 80 with a high level corresponding approximately to the operating voltage, while the fourth output signal 82 permanently has a signal level corresponding approximately to the ground level at the connection pin 58.

In one preferred exemplary embodiment, the sensor arrangement 18 is able to detect three different actuators using the corresponding input signals 66 and, on the basis thereof, to generate different signal pairs at the connection pins 68, 70. In one exemplary embodiment, the sensor arrangement implements the following logic table:

| E1 | E2 | E3 | A1 | A2 |
|----|----|----|----|----|
| 0  | 0  | 0  | 0  | 0  |
| 0  | 0  | 1  | 0  | 1  |
| 0  | 1  | 0  | 1  | 0  |
| 0  | 1  | 1  | 0  | 0  |
| 1  | 0  | 0  | 1  | 1  |
| 1  | 0  | 1  | 0  | 0  |
| 1  | 1  | 0  | 0  | 0  |
| 1  | 1  | 1  | 0  | 0  |

In this case, E1 denotes a first input signal which signals a safety-relevant installation state, for example the closed guard door 24. E2 and E3 are non-safety-relevant input signals which represent further states, for instance the operating position of the transport carriage 14 or an operator signal generated with the aid of the actuator 22d. As can be discerned using the above table, the sensor arrangement 18 exclusively generates the redundant signal pair with two active signal levels when only the first input signal E1 is received. As soon as more than one input signal is received, the evaluation unit generates only the passive signal levels, which are symbolized by "0" in the table, at the connection pins 68, 70. If only the second input signal E2 is received, the sensor arrangement 18 generates an active signal level at the connection pin 68 with the aid of the first switching element 74a, while a passive signal level is generated at the connection pin 70. In this manner, the sensor arrangement can inform the higher level controller 28 that the further input signal E2 has been detected. This may come from the actuator 22a, for example.

In a corresponding manner, the sensor arrangement 18 generates a passive signal level at the connection pin 68 and an active signal level at the connection pin 70 when only the third input signal, for example from the actuator 22b, has been detected.

Overall, the novel sensor arrangement 18 can thus generate a safety-relevant, redundant signal pair and alternatively two non-redundant signal pairs at the connection pins 68, 70. On the basis of the first input signal or a further input signal, the novel sensor arrangement accordingly provides different signal pairs on the redundant output lines 40, 42 or 44, 46. The sensor part 20 of the sensor arrangement 18 can therefore be used either as a safety sensor for monitoring the guard door 24 or as a standard sensor for determining the operating position of a movable part, the same connection pins 68, 70 being used in each case. In one preferred exemplary embodiment, the sensor arrangement 18 has a connecting plug (male or female) in which all connection pins required are integrated. In some exemplary embodiments, the connecting plug is a 6-pole or 8-pole plug, i.e. the sensor arrangement has a maximum of eight connection pins. All exemplary embodiments of the novel sensor arrangement preferably have a defined number of connection pins which is limited on the basis of the dimensions of the device housing 54 and/or on the basis of the dimensions of a common connecting plug. In particular, the number of connection pins at which the novel sensor arrangement can output signals is precisely two in preferred exemplary embodiments.

In one variant of the exemplary embodiment shown in FIG. 1, the operator 26 can use the actuator 22d to transmit a standard control signal to the controller 28 after he has opened the guard door 24. For example, the operator can use the actuator 22d to transmit a control command to the controller 28 via the safety lines 40, 42, the controller 28 giving rise to a defined operating position of the robot 12, which facilitates a maintenance operation, on the basis of the standard control command. In contrast to previous installations, the operator 26 can transmit the standard control command to the controller 28 via the safety-relevant sensor arrangement 18" after the sensor arrangement 18" has previously cancelled the redundant signal pair 76, 78 and the controller 28 has accordingly interrupted the power supply 36 for the robot 12. The sensor arrangement 18 consequently transmits the non-redundant signal pair and the redundant signal pair in temporally successive intervals. In another exemplary embodiment, the connection pin 72 can be used to supply the further input signal, i.e. the evaluation unit 64a, 64b is designed in this case to generate a non-redundant signal pair 80, 82 when it receives a corresponding input signal via the connection pin 72.

In other exemplary embodiments, the sensor arrangement 18 can integrate the respective identification code 62a, 62c in the output signals at the connection pins 68, 70, in particular in the form of a binary code with successive bits.

What is claimed is:

1. In an installation operated in an automated manner under the control of at least one control unit, said installation having a plurality of operational states and at least one safety-related state, a sensor arrangement comprising:
    an input circuit designed to receive a first input signal depending on the safety-related state and designed to receive at least one further input signal depending on one of said plurality of operational states,
    a first output and at least one second output for outputting a first output signal and a second output signal to the at least one control unit, and
    an evaluation unit designed to evaluate the first input signal in a fail-safe manner and, on the basis thereof, to generate the first and second output signals at the first and second outputs, with the first and second output signals forming a redundant signal pair which in combination signals the safety-related state to the control unit,
    wherein the evaluation unit is further designed to evaluate the further input signal and, on the basis thereof, to generate a third output signal at the first output and a fourth output signal at the second output, with the third and fourth output signals forming a non-redundant signal pair which differs from the redundant signal pair, and further
    wherein the evaluation unit generates the redundant signal pair with the first and second output signals if and only if the input circuit receives only the first input signal.

2. The sensor arrangement of claim 1, wherein the output signals at the first and second outputs each are binary signals having either an active first signal level or a passive second signal level, with the first and second output signals each having the active first signal level.

3. The sensor arrangement of claim 2, wherein the third output signal or the fourth output signal corresponds to the passive second signal level.

4. The sensor arrangement of claim 1, wherein the first and second output signals each have recurring changing signal levels.

5. The sensor arrangement of claim 1, wherein the evaluation unit generates the redundant signal pair and the non-redundant signal pair in temporally successive intervals.

6. The sensor arrangement of claim 1, further comprising a device housing, in which the input circuit and the evaluation unit are arranged, and comprising at least one actuator which is spatially separate from the device housing and generates one of the input signals.

7. The sensor arrangement of claim 6, wherein the actuator has an individual identification code which is transmitted to the evaluation unit via said one of the input signals.

8. The sensor arrangement of claim 7, wherein the evaluation unit integrates the individual identification code in at least one of the output signals.

9. The sensor arrangement of claim 6, wherein the at least one actuator comprises a first actuator with a first individual identification code and at least one further actuator with a further individual identification code, with the evaluation unit distinguishing the first input signal from the further input signal on the basis of the first individual identification code and the further individual identification code.

10. The sensor arrangement of claim 1, further comprising a cable connection for supplying the further input signal.

11. A sensor arrangement for detecting a safe installation state of an installation operated in an automated manner, the sensor arrangement comprising:
    an input circuit designed to receive a first input signal and designed to receive at least one further input signal, with the first input signal depending on the safe installation state to be detected, and with the further input signal depending on a further state,
    a first output and at least one second output for outputting a first output signal and a second output signal, and
    an evaluation unit designed to evaluate the first input signal in a fail-safe manner and, on the basis thereof, to generate the first and second output signals at the first and second outputs, with the first and second output signals forming a redundant signal pair which in combination signals the safe installation state,
    wherein the evaluation unit is further designed to evaluate the further input signal and, on the basis thereof, to generate a third output signal at the first output and a fourth output signal at the second output, with the third and fourth output signals forming a non-redundant signal pair which differs from the redundant signal pair, and further wherein the evaluation unit generates the redundant signal pair with the first and second output signals only when the input circuit exclusively receives the first input signal.

12. The sensor arrangement of claim 11, wherein the output signals at the first and second outputs each are binary signals having either an active first signal level or a passive second signal level, with the first and second output signals each having the active first signal level.

13. The sensor arrangement of claim 12, wherein at least one from the third output signal and the fourth output signal corresponds to the passive second signal level.

14. The sensor arrangement of claim 11, wherein the first and second output signals each have periodically changing signal levels.

15. The sensor arrangement of claim 11, wherein the evaluation unit generates the redundant signal pair and the non-redundant signal pair in successive time intervals.

16. The sensor arrangement of claim 11, further comprising a device housing, in which the input circuit and the evaluation unit are arranged, and comprising at least one actuator which is spatially separate from the device housing and generates one of the input signals.

17. The sensor arrangement of claim 16, wherein the at least one actuator comprises a first actuator with a first individual identification code and at least one further actuator with a further individual identification code, with the evaluation unit distinguishing the first input signal from the further input signal on the basis of the first individual identification code and the further individual identification code.

18. The sensor arrangement of claim 17, wherein the evaluation unit integrates at least one from the individual identification codes in at least one of the output signals.

19. In an installation operated in an automated manner under the control of at least one control unit, said installation having a plurality of operational states and at least one safety-related state, a sensor arrangement comprising:

an input circuit designed to receive a first input signal depending on the safety-related state and designed to receive at least one further input signal depending on one of said plurality of operational states, a first output and at least one second output for outputting a first output signal and a second output signal to the at least one control unit, and an evaluation unit designed to evaluate the first input signal in a fail-safe manner when identified as an input signal relating to a safety-related state of said installation and, on the basis thereof, generate the first and second output signals at the first and second outputs, with the first and second output signals forming a redundant signal pair which in combination signals the safety-related state to the control unit, and wherein the evaluation unit is further designed to evaluate the further input signal and, when identified as an input signal relating to one of said plurality of operational states of said installation, on the basis thereof, generate a third output signal at the first output and a fourth output signal at the second output, with the third and fourth output signals forming a non-redundant signal pair which differs from the redundant signal pair, wherein the evaluation unit generates the redundant signal pair with the first and second output signals if and only if the input circuit receives only the first input signal.

20. A sensor arrangement for detecting a safety-related state of an installation operated in an automated manner, the sensor arrangement comprising:

an input circuit designed to receive a first input signal and designed to receive at least one further input signal, with the first input signal depending on the safety-related state of the installation, and with the further input signal depending on an operational state of the automated installation, a first output and at least one second output for outputting a first output signal and a second output signal, and an evaluation unit designed to evaluate the first input signal in a fail-safe manner when identified as an input signal relating to a safety-related state of said installation and, on the basis thereof, generate the first and second output signals at the first and second outputs, with the first and second output signals forming a redundant signal pair which in combination signals the safety-related state, wherein the evaluation unit is further designed to evaluate the further input signal and, when identified as an input signal relating to the operational state of said installation, on the basis thereof, generate a third output signal at the first output and a fourth output signal at the second output, with the third and fourth output signals forming a non-redundant signal pair which differs from the redundant signal pair, wherein the evaluation unit generates the redundant signal pair with the first and second output signals only when the input circuit exclusively receives the first input signal.

* * * * *